United States Patent [19]

Mori et al.

[11] Patent Number: 5,663,461

[45] Date of Patent: Sep. 2, 1997

[54] PROCESS FOR PRODUCING GERANYLGERANIOL

[75] Inventors: Toshiki Mori, Kurashiki-machi; Junko Sato, Niigata-ken; Takashi Fukumoto, Kyowa-machi; Kozo Nakao, Yokohama; Yoshin Tamai, Shibata, all of Japan

[73] Assignee: Kuraray Co., Ltd., Kurashiki, Japan

[21] Appl. No.: 554,405

[22] Filed: Nov. 6, 1995

[30] Foreign Application Priority Data

Aug. 11, 1994 [JP] Japan .................... 6-298857

[51] Int. Cl.⁶ .................................. C07C 29/09
[52] U.S. Cl. .................. 568/886; 558/355; 558/211; 560/20; 560/8
[58] Field of Search .................. 558/355, 211; 560/8, 20; 568/880

[56] References Cited

FOREIGN PATENT DOCUMENTS 54-55506  4/1979  Japan .................... 568/886

OTHER PUBLICATIONS

Synletters, p. 783 (1993).

*Primary Examiner*—James H. Reamer
*Attorney, Agent, or Firm*—Oblon, Spivak, McClelland, Maier & Neustadt, P.C.

[57] ABSTRACT

A process for producing geranylgeraniol is provided, which comprising the steps of subjecting a mixture of at least one ester derivative wherein one or more carbon-carbon double bonds in the molecule are in cis form represented by the general formula (1):

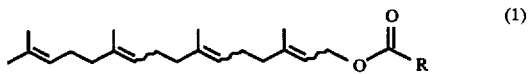

wherein R represents an aromatic group which can be substituted with at least one substituent, or a higher aliphatic group having from 7 to 25 carbon atoms, and wavy lines, respectively, represent a state where each carbon-carbon double bond can be present in cis or trans form, and an ester derivative of the general formula (2):

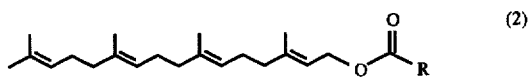

wherein R is as defined above, to crystallization to obtain the ester derivative of the formula (2) selectively, and hydrolyzing the thus obtained ester derivative.

10 Claims, No Drawings

PROCESS FOR PRODUCING GERANYLGERANIOL

BACKGROUND OF THE INVENTION

1. Field of the Invention

The present invention relates to a process for producing 3,7,11,15-tetramethylhexadeca-2E,6E,10E, 14-tetraenol (hereinafter referred to simply as "geranylgeraniol").

The geranylgeraniol obtained by the present invention are useful as starting materials for producing vitamin K2, tocotrienol and so on.

2. Related Art of the Invention

Known processes for producing geranylgeraniol include, for example, (1) a process wherein trialkylphosphonoacetates are reacted with farnesylacetone, followed by reduction of the resultant compound with aluminium hydride [SYNLETT 783 (1993)], and (2) a process wherein geranyl p-toluenesulfonate is reacted with 8-bromogeranyl acetate using n-butyl lithium, followed by de-sulfonation with metallic lithium and amines (Japanese Patent Laid-open No. Sho 54-55506).

The geranylgeraniol obtained by these processes includes geometrical isomers wherein one or more of the carbon-carbon double bonds in the molecule are in cis form. Therefore, it is necessary to purify the mixture through precise distillation or column chromatography in order to obtain pure geranylgeraniol, whose carbon-carbon double bonds are all in trans form. However, geranylgeraniol has a high boiling point and an ally alcohol structure which is thermally unstable, so that the precise distillation of geranylgeraniol is extremely difficult. On the other hand, the purification of geranylgeraniol through column chromatography needs not only large amounts of solvents and packing materials such as silica gel, but also the preparation of a developing solvent and successive analysis of eluted fractions in relation to time. In the latter case, it is necessary that a desired fraction or fractions should be collected based on the analysis, after which the solvent has to be removed. Thus, the purification of geranylgeraniol with column chromatography requires very complicated operations, and are not suitable for industrial applications.

SUMMARY OF THE INVENTION

An object of the present invention is to provide an industrially useful process for producing geranylgeraniol in an easy and simple manner.

The object of the present invention can be achieved by the present invention described below.

More particularly, the present invention provides a process for producing geranylgeraniol comprising the steps of subjecting a mixture of at least one ester derivative wherein one or more carbon-carbon double bonds in the molecule are in cis form represented by the general formula (1):

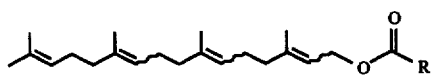

wherein R represents an aromatic group which may have at least one substituent, or a higher aliphatic group having from 7 to 25 carbon atoms, and wavy lines, respectively, represent a state where each carbon-carbon double bond can be present in cis or trans form, and an ester derivative of the general formula (2):

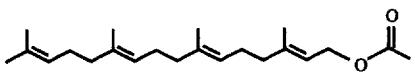

wherein R is as defined above, to crystallization in order to obtain the ester derivative of the formula (2) selectively, and hydrolyzing the thus obtained ester derivative.

DETAILED DESCRIPTION OF THE INVENTION

The present invention is described in more detail.

The ester derivatives of the formulae (1) and (2) are described. In the formulae (1) and (2), R represents an aromatic group which can be substituted with at least one substituent, or a higher aliphatic group having from 7 to 25 carbon atoms. The aromatic groups represented by R include, for example, a phenyl group, a naphthyl group, an anthryl group, a pyridyl group, a furyl group and the like. These aromatic groups can be substituted with at least one substituent. Examples of the substituent include lower alkyl groups such as a methyl group, an ethyl group, a n-propyl group, an i-propyl group, a n-butyl group and a t-butyl group; halogen atoms such as chlorine, bromine and iodine; a carboxyl group; alkoxycarbonyl groups such as a methoxycarbonyl group and an ethoxycarbonyl group; acyl groups such as an acetyl group and a benzoyl group; alkoxy groups such as a methoxy group and an ethoxy group; a nitrile group; a nitro group; alkylsulfonyl groups such as a methylsulfonyl group and an ethylsulfonyl group; arylsulfonyl groups such as a p-toluenesulfonyl group and a phenylsulfonyl group; an amino group; alkylamino groups such as a dimethylamino group, a methylamino group and an ethylamino group; and a hydroxy group. The aromatic group may have one or more substituents set out hereinabove.

The higher aliphatic groups having from 7 to 25 carbon atoms and represented by R include alkyl groups such as a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-icosyl group and a henicosyl group; alkenyl groups such as a 1-decenyl group, an 8-hexadecenyl group and an 8,11-heptadecadienyl group; and an alkynyl group such as a 1-undecynyl group.

Specific examples of the ester derivatives of the formula (2) wherein R represents an aromatic group which can be substituted with at least one substituent include geranylgeranyl benzoate, geranylgeranyl 1-naphthylcarboxylate, geranylgeranyl 3-naphthylcarboxylate, geranylgeranyl 9-anthracenecarboxylate, geranylgeranyl tolylate, geranylgeranyl p-methoxycarbonylbenzoate, geranylgeranyl o-hydroxycarbonylbenzoate, geranylgeranyl p-phenylcarbonylbenzoate, geranylgeranyl p-methoxybenzoate, geranylgeranyl m-nitrobenzoate, geranylgeranyl p-nitrobenzoate, geranylgeranyl o-nitrobenzoate, geranylgeranyl m,m-dinitrobenzoate, geranylgeranyl p-phenylsulfonylbenzoate, geranylgeranyl p-methylsulfonylbenzoate, geranylgeranyl dimethylaminobenzoate, geranylgeranyl p-aminobenzoate, geranylgeranyl p-cyanobenzoate, geranylgeranyl p-hydroxybenzoate, geranylgeranyl nicotinate, geranylgeranyl 2-furylcarboxylate, and the like.

Specific examples of the ester derivatives of the formula (2) wherein R represents a higher aliphatic group with 7 to 25 carbon atoms include geranylgeranyl octate, geranylgeranyl laurate, geranylgeranyl myristate, geranylgeranyl stearate, geranylgeranyl oleate, geranylgeranyl linoleate, geranylgeranyl 11-undecenate, geranylgeranyl 11-undecynate and the like.

In the practice of the present invention, the mixture of the ester derivatives of the formulae (1) and (2) can be prepared as follows. A mixture of an alcohol of the following formula (3) wherein the wavy lines are, respectively, as defined hereinbefore and wherein one or more carbon-carbon double bonds in the molecules are in cis form, and a geranylgeraniol, which is obtained by the reaction set forth in the afore-mentioned document [SYNLETT 783(1993)] or Japanese Patent Laid-open No. Sho 54-55506, is reacted with a carboxylic acid derivative either of the following formula (4) wherein R is as defined hereinbefore and X represents a halogen atom or a hydroxy group, or of the following formula (5) wherein R is as defined hereinbefore and R' is the same substituent as R or represents a lower alkyl group such as a methyl group, an ethyl group, a propyl group, an i-propyl group or a t-butyl group.

The reaction sequence is shown below:

moles per mole of the mixture together with an esterifying agent, e.g., N-methyl-2-chloropyridinium iodide, N, N-dimethylchloroiminium chloride or the like, in not less than an equimolar amount of the carboxylic acid derivative. The esterification reaction is carried out in an organic solvent, e.g., benzene, toluene, methylene chloride, chloroform, i-propyl ether, tetrahydrofuran, n-hexane, cyclohexane, N, N-dimethylformamide, N-methylpyrrolidone or the like, in an amount by weight of 1 to 200 times that of the mixture of the alcohol of the formula (3) and the geranylgeraniol at a temperature of from 0° to 100° C. The esterification reaction is performed in the presence of an amine, e.g., trimethylamine, triethylamine, tributylamine, pyridine or the like, in not less than an equimolar amount relative to the carboxylic acid derivative.

The resultant reaction mixture of the esterification is after-treated as follows: water is added to the reaction mixture to stop the reaction; the product is extracted with a solvent such as hexane, toluene, diethyl ether, i-propyl ether or methylene chloride; and the resultant extract is washed with diluted hydrochloric acid, water and an aqueous

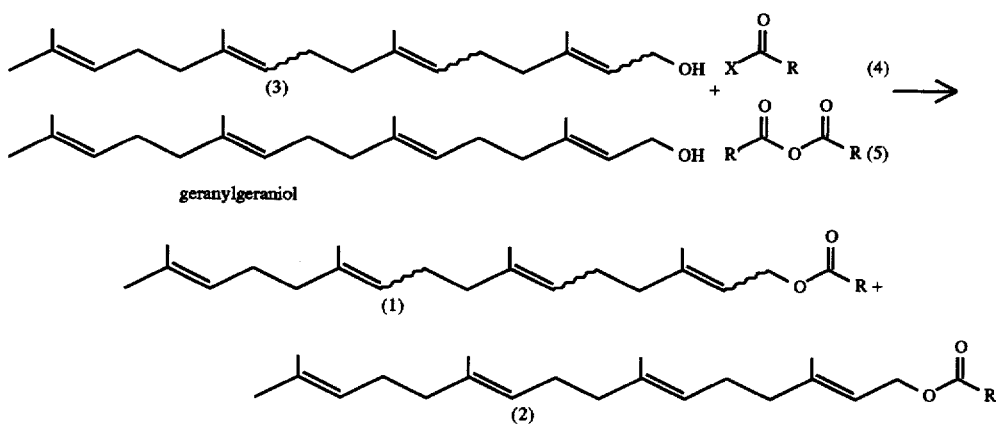

For the above esterification reaction with the carboxylic acid derivative of the formula (4) where X is a halogen atom such as chlorine, bromine, iodine, or with the carboxylic acid derivative of the formula (5), the carboxylic acid derivative is used in an amount of 1 to 3 moles per mole of the mixture of the alcohol of the formula (3) and the geranylgeraniol. The esterification reaction is carried out in an organic solvent, e.g., benzene, toluene, methylene chloride, chloroform, i-propyl ether, tetrahydrofuran, n-hexane, cyclohexane or the like, in an amount by weight of 1 to 200 times that of the mixture in the presence of not less than an equimolar amount, relative to the carboxylic acid derivative, of an amine such as triethylamine, tributylamine, pyridine or the like, at a temperature of from 0° to 100° C.

The above esterification reaction with the carboxylic acid derivative of the formula (4) where X is a hydroxy group is carried out in the following manner. The carboxylic acid derivative is added to the mixture of the alcohol of the formula (3) and the geranylgeraniol in an amount of 1 to 3 sodium bicarbonate successively, followed by removal of solvent. The resultant mixture of the ester derivatives of the formulae (1) and (2) can be used as it is in the practice of the present invention.

Alternatively, the mixture of the ester derivatives of the formulae (1) and (2) can be prepared from 3,7,11,15-tetramethyl-hexadeca-1,6E,10E, 14E-tetraen-3-ol (hereinafter referred to simply as "geranyllinalool") in the following manner. Geranyllinalool is first halogenated to obtain a mixture of a halogenated derivative of the following formula (6) wherein Y represents a halogen atom such as chlorine, bromine, iodine or the like and a halogenated derivative of the following formula (7) wherein Y is as defined above, followed by further reaction with a metal carboxylate wherein R is as defined hereinbefore and M represents an alkali metal such as sodium, potassium, lithium or the like.

The reaction sequence is shown below:

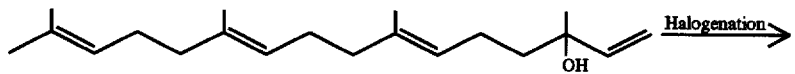

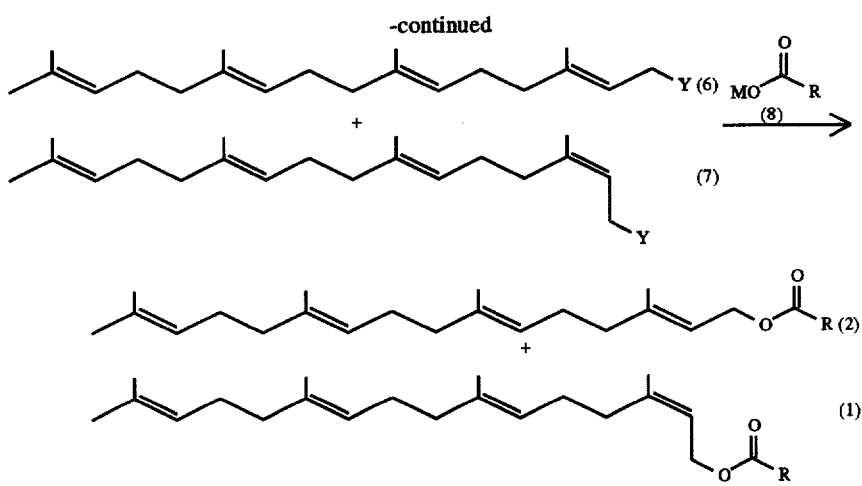

In the above sequence, geranyllinalool is halogenated, in an organic solvent, e.g., benzene, toluene, methylene chloride, chloroform, i-propyl ether, tetrahydrofuran, n-hexane, cyclohexane or the like, in an amount by weight of 1 to 200 times that of the geranyllinalool, with a halogenating agent, e.g., phosphorus trichloride, phosphorus tribromide, phosphorus triiodide, phosphorus pentachloride, thionyl chloride, thionyl bromide, oxalyl chloride or the like, in an amount of ⅓ to 2 moles per mole of the geranyllinalool at a temperature of from −20° to 60° C.

When thionyl chloride, thionyl bromide or oxalyl chloride is used as halogenating agent, it is preferred to add an amine such as trimethylamine, triethylamine, tributylamine, pyridine or the like to the reaction system in not less than an equimolar amount relative to the halogenating agent. The reaction mixture is after-treated by addition of water to stop the reaction. Thereafter, the product is extracted with a solvent such as toluene, n-hexane, diethyl ether, i-propyl ether or methylene chloride. The resultant extract is washed with water and an aqueous sodium bicarbonate successively, followed by removal of the solvent.

The resulting mixture of the halogenated derivatives of the formulae (6) and (7) can be converted to a mixture of the ester derivatives of the formulae (1) and (2) through reaction with the metal carboxylate of the formula (8). This reaction is carried out in a solvent, e.g., benzene, toluene, n-hexane, cyclohexane, n-pentane, tetrahydrofuran, i-propyl ether or the like, in an amount by weight of ½ to 200 times that of the mixture of the halogenated derivatives of the formulae (6) and (7) in the presence of a phase-transfer catalyst, in an amount of 0.2–10 mol % of the halogenated derivatives at a temperature of from 40° to 150° C. Examples of the phase-transfer catalysts include n-tetrabutylammonium chloride, n-tetrabutylammonium bromide, n-tetrabutylammonium iodide, stearyltrimethylammonium chloride, stearyltrimethylammonium bromide, stearyltrimethylammonium iodide and the like.

The metal carboxylate of the formula (8) is used in an amount of 1 to 3 moles per mole of the halogenated derivatives of the formulae (6) and (7). The reaction mixture is cooled down to room temperature. Thereafter water is added to the reaction mixture. Then the product is extracted with a solvent such as a toluene, n-hexane, diethyl ether, i-propyl ether or methylene chloride. The resultant extract is washed with diluted hydrochloric acid, water and an aqueous sodium bicarbonate successively, followed by removal of the solvent. The mixture of the ester derivatives of the formulae (1) and (2) can be used as it is in the practice of the present invention.

The mixture of the ester derivatives of the formulae (1) and (2) are then crystallized to obtain an ester derivative of geranylgeraniol of the formula (2) selectively.

The solvents used for the crystallization include alcohol solvents such as methanol, ethanol, i-propanol, n-butanol and methyl cellosolve; aliphatic solvents such as n-hexane, cyclohexane and n-heptane; aromatic solvents such as benzene, toluene and xylene; halogenated solvents such as methylene chloride and chloroform; ester solvents such as ethyl acetate and butyl acetate; and ether solvents such as diethyl ether, isopropyl ether and methyl t-butyl ether. The solvents most suitable for the crystallization should be properly selected from the standpoint of the solubility of the mixture to be crystallized, the amount of solvent, the filtration temperature and so on. Ordinarily alcohol solvents such as methanol, ethanol, i-propanol and n-butanol, an aliphatic solvent such as n-hexane, and an aromatic solvent such as toluene are used for the crystallization. Of these, the alcohols such as methanol, ethanol, i-propanol and n-butanol are preferred.

These solvents can be used alone or in combination. The amount by weight of the solvent generally ranges from ⅓ to 100 times that of the mixture of the ester derivatives of the formulae (1) and (2). If the mixture of the ester derivatives of the formulae (1) and (2) is unlikely to dissolve depending on the type and amount of the solvent used, it can be dissolved by heating.

After the dissolution of the mixture of the ester derivatives of the formulae (1) and (2) in a solvent, the resultant solution is gradually cooled down in order to permit crystals to precipitate. On the way of the cooling, seed crystals of the target ester derivative to be crystallized may be added in small amounts with some possibility that crystals of higher purity are obtained.

The thus precipitated crystals are separated by any known procedures such as filtering operations using filter paper, filter cloth or a glass filter. Although the crystals may be separated at a temperature at which the crystals are precipitated, they are obtained in greater amounts when the separation is carried out at temperatures lower by 1° to 50° C. than the precipitation temperature.

According to the crystallization set out above, the ester derivative of geranylgeraniol of the formula (2) is crystallized or obtained in the form of a concentrated solution. If the ester derivative of geranylgeraniol of the formula (2) has a purity lower than an intended level, similar crystallization can be repeated, thereby increasing its purity. Thus, the ester derivative of geranylgeraniol of the formula (2) can be obtained selectively from the mixture with its geometrical isomer which has one or more carbon-carbon double bonds of a cis form in the molecule.

The ester derivative of geranylgeraniol of the formula (2) obtained by the crystallization is converted to geranylgeraniol through hydrolysis.

The hydrolysis is carried out under ordinary conditions. For instance, the ester derivative of geranylgeraniol of the formula (2) is hydrolyzed in an alcohol solvent, e.g., methanol, ethanol, i-propanol, n-butanol or the like, in an amount by weight of 0.5 to 200 times that of the ester derivative of geranylgeraniol, with an aqueous solution of alkali metal hydroxide or alkali earth metal hydroxide with a concentration of about 0.5% to 50% under the condition that the hydroxide is present in an amount of 1 to approximately 10 moles per mole of the ester derivative of geranylgeraniol. Examples of the alkali metal hydroxide or alkaline earth metal hydroxide include sodium hydroxide, potassium hydroxide, lithium hydroxide, barium hydroxide and the like. The hydrolysis reaction is conducted at a temperature ranging from 0° to 150° C., preferably from 20° to 80° C. Generally, the hydrolysis reaction is completed within a range of one minute to about 5 hours.

After the completion of the hydrolysis, water and an organic solvent such as toluene, hexane, diethyl ether or i-propyl ether are, respectively, added to the reaction mixture in amounts by weight of 1 to 10 times that of the alcohol solvent used. The resulting organic phase is separated and washed with water, followed by removal of solvent. If desired, the resultant residue is distilled under reduced pressure to give a geranylgeraniol of high purity. It will be noted that in the after-treatment for the hydrolysis of the ester derivative of geranylgeraniol of the formula (2) wherein R is a higher aliphatic group, the solution obtained after addition of water and an organic solvent to the reaction mixture may be in the form of an emulsion, resulting in the failure of the separation of organic phase. To cope with this, methanol is used for the solvent in hydrolysis while employing a minimum amount of water, under which the ester derivative of geranylgeraniol is hydrolyzed. Thereafter, the hydrolyzed product is repeatedly extracted with an aliphatic solvent such as hexane. By this, geranylgeraniol can be readily obtained.

According to the present invention, geranylgeraniol, useful as a starting material for the preparation of vitamin K2, tocotrienols and so on, can be readily produced in an easy and simple manner as will not be achieved by prior art. Thus, the present invention is very useful for industrial production of geranylgeraniol.

Other features of the present invention will become apparent in the course of the following descriptions of exemplary embodiments which are given for illustration of the present invention and are not rendered to be limiting thereof.

EXAMPLES

In ensuing examples and references, the purity of compounds is intended to mean a content (wt %) of a compound in a mixture.

Reference 1 (Preparation of a mixture of geranylneryl stearate/geranylgeranyl stearate from geranyllinalool)

10 ml (105 mmols) of phosphorus tribromide was gradually added to 500 ml of a solution of 87 g (300 mmols) of geranyllinalool in i-propyl ether at 0°. The mixture was stirred at the same temperature for 100 minutes. 300 ml of water was added to reaction mixture and the resulting organic phase was separated and washed with 200 ml of water, 200 ml of a 2% aqueous sodium bicarbonate and 200 ml of water successively, followed by removal of the solvent under reduced pressure to give 122.87 g of a residual oil. 88.6 g of the thus obtained oil was gradually added, at 110° C., into 250 g of a toluene solution containing sodium stearate, which was prepared from 70 g (246 mmols) of stearic acid and 47.44 g (246 mmols) of 28% methanolic sodium methoxide, and 4.03 g of tetrabutylammonium bromide. The mixture was stirred at the same temperature for 1 hour. After cooling down to room temperature, the precipitate was removed with a glass filter and the filtrate was washed with 100 ml of water and 100 ml of a 2% aqueous sodium bicarbonate successively, followed by removal of the solvent under reduced pressure to give 110.93 g of a residual oil. The results of HPLC analysis of the product revealed that it contained 27.07 g (48.6 mmols) of geranylneryl stearate with a purity of 24.4% and 66.89 g (120.2 mmols) of geranylgeranyl stearate with a purity of 60.3%. Part of the thus obtained oil was used as it is in Example 1 appearing hereinafter.

The conditions of the HPLC analysis are as follows.

Column: Licrosorb Si-60, 250 mm×4 mm (made by GL Science INC.)

Solvent: methyl t-butyl ether/iso-octane=1.5/98.5 (v/v), 0.5 ml/minute

Detector: 210nm UV detector

Internal standard: diphenyl

Reference 2 (Preparation of a mixture of geranylneryl palmitate/geranylgeranyl palmitate from a mixture of geranylnerol/geranylgeraniol and palmitic acid in the presence of N-methyl-2-chloropyridinium iodide)

100 ml of a methylene chloride solution of 20.5 g (80 mmols) of N-methyl-2Chloropyridinium iodide was gradually added, at room temperature, to 150 ml of a methylene chloride solution containing 16.52 g of a mixture of 4.57 g (15.76 mmols) of geranylnerol with a purity of 27.7% and 9.30 g (32.07 mmols) of geranylgeraniol with a purity of 56.3%, 15.4 g (60 mmols) of palmitic acid and 5.53 g (70 mmols) of pyridine. The mixture was refluxed for 5 hours. After cooling down to room temperature, 100 ml of water was added to the reaction mixture and the resulting organic phase was separated and washed with 150 ml of 5% hydrochloric acid, 150 ml of water, 150 ml of a 2% aqueous sodium bicarbonate and 150 ml of water successively, followed by removal of the solvent under reduced pressure to give 23.42 g of a residual oil. The results of HPLC analysis of the product revealed that it contained 6.65 g (12.59 mmols) of geranylneryl palmitate with a purity of 28.4% and 13.5 g (25.66 mmols) of geranylgeranyl palmitate with a purity of 57.9%. The oil was used in Example 3 appearing hereinafter.

The conditions of HPLC analysis are those as used in Reference 1.

Reference 3 (Preparation of a mixture of geranylneryl p-nitrobenzoate/geranylgeranyl p-nitrobenzoate from geranyllinalool)

10 ml (105 mmols) of phosphorus tribromide was gradually added to a solution of 87 g (300 mmols) of geranyllinalool in 500 ml of i-propyl ether. The mixture was stirred at the same temperature for 3 hours. 300 ml of water was added to the reaction mixture and the resulting organic phase was separated and washed with 200 ml of water, 200 ml of a 2% aqueous sodium bicarbonate and 200 ml of water successively, followed by removal of the solvent under reduced pressure to give 110.86 g of a residual oil. The thus obtained oil was gradually added, at 110° C, to a suspension of 56.7 g (300 mmols) of sodium p-nitrobenzoate and 1.93 g (6 mmols) of tetrabutylammonium bromide in 500 ml of toluene. The mixture was stirred at the same temperature for 2 hours. After cooling down to room temperature, the precipitate was removed with a glass filter and the filtrate was washed with 200 ml of water, 200 ml of a 2% aqueous sodium bicarbonate and 200 ml of water successively, followed by removal of the solvent under reduced pressure to give 137.63 g of a residual oil. The results of HPLC analysis of the product revealed that it contained 28.9 g (66 mmols) of geranylneryl p-nitrobenzoate with a purity of 21.0% and 76.39 g (174 mmols) of geranylgeranyl p-nitrobenzoate with a purity of 55.5%. Part of the thus obtained oil was used as it is in Examples 8 and 9 appearing hereinafter.

The conditions of HPLC analysis are as follows.

Column: Licrosorb Si-60, 250 mm×4 mm (made by GL Science INC.)

Solvent: methyl t-butyl ether/iso-octane=5/95 (v/v), 0.5 ml/minute

Detector: 220 nm UV detector

Internal standard: benzophenone

Reference 4 (Preparation of a mixture of geranylneryl p-methoxycarbonylbenzoate/geranylgeranyl p-methoxycarbonylbenzoate from a mixture of geranylnerol/geranylgeraniol and p-methoxycarbonylbenzoyl chloride)

20 ml of tetrahydrofuran solution of 9.53 g (48 mmols) of p-methoxycarbonylbenzoyl chloride was gradually added, at room temperatuere, to 50 ml of a tetrahydrofuran solution containing 12.0 g of a mixture of 4.3 g (14.83 mmols) of geranylnerol with a purity of 35.8% and 7.32.g (25.2 mmols) of geranylgeraniol with a purity of 61.0%, and 3.80 g (48 mmols) of pyridine. The mixture was refluxed for 3 hours. After cooling down to room temperature, 100 ml of n-hexane and 100 ml of water were added to the reaction mixture and the resulting organic phase was separated and washed with 100 ml of a 5% aqueous hydrochloric acid, 100 ml of water, 100 ml of a 2% aqueous sodium bicarbonate and 100 ml of water successively, followed by removal of the solvent under reduced pressure to give 19.27 g of a residual oil. The results of HPLC analysis of the product revealed that it contained 5.55 g of geranylneryl p-methoxycarbonylbenzoate with a purity of 28.8% and 9.45 g of geranylgeranyl p-methoxycarbonylbenzoate with a purity of 49.0%. The thus obtained oil was used as it is in Example 10 appearing hereinafter.

The conditions of HPLC analysis are as follows.

Column: Licrosorb Si-60, 250 mm×4 mm (made by GL Science INC.)

Solvent: methyl t-butyl ether/iso-octane=1.5/98.5 (v/v), 1.5 ml/minute

Detector: 220 nm UV detector

Internal standard: benzophenone

Example 1

(crystallization of geranylgeranyl stearate: first time)

67.0 g of a mixture of 16.35 g of geranylneryl stearate (purity: 24.4%) and 40.4 g of geranylgeranyl stearate (purity: 60.3%) was dissolved in 512 g of ethanol at room temperature. The solution was cooled gradually, to which geranylgeranyl stearate (seed crystal) was added in small amounts to make crystals precipitated, followed by cooling down further to 2.7° C. Thereafter, the precipitates were filtered at the same temperature as indicated above and the obtained cake (precipitates) was rinsed with a small amount of cooled ethanol. The ethanol rinsings were added to the filtrate. The cake obtained was dried under reduced pressure at room temperature to give 35.8 g of oil. The results of HPLC analysis of the product revealed that it contained 31.2 g of geranylgeranyl stearate with a purity of 87.2% and 3.78 g of geranylneryl stearate with a purity of 10.6%.

The HPLC analysis conditions are those as used in Reference 1.

Moreover, 28.13 g of a residual oil was obtained through concentration of the filtrate, which contained 8.9 g of geranylgeranyl stearate with a purity of 31.6% and 12.44 g of geranylneryl stearate with a purity of 44.2%

Example 2

(crystallization of geranylgeranyl stearate: second time)

35.8 g of the oil (containing 31.2 g of geranylgeranyl stearate) obtained in Example 1 was dissolved in 450 g of ethanol, followed by crystallization in the same manner as in Example 1 to give 26.67 g of oil from the cake (precipitates) which contained 25.61 g of geranylgeranyl stearate with a purity of 96% and 0.418 g of geranylneryl stearate with a purity of 1.6%, and 12.0 g of a residual oil from the filtrate which contained 5.52 g of geranylgeranyl stearate with a purity of 46.0% and 3.30 g of geranylneryl stearate with a purity of 27.5%. The oil obtained from the cake was crystallized at 11.4° C. to 12° C.

[$^1$H-NMR data of cake (geranylgeranyl stearate)]

$^1$H-NMR [δ(ppm), 300 MHz, CDCl$_3$]

0.89(t, J=7.0 Hz, 3H), 1.26(s, 30H), 1.61(s, 9H), 1.68(s, 3H), 1.71(s, 3H), 1.98–2.15(m, 12H), 2.30(t, J=7.4 Hz, 2H), 4.60(d, J=7.1 Hz, 2H), 5.11(m, 3H), 5.32(t, J=7.1 Hz, 1H)

Examples 3 to 13

Various ester derivatives were crystallized in the same manner as in Example 1, and the results are shown in Tables 1 to 4.

TABLE 1

| | Starting material for crystallization gross weight and components | Solvent weight filtration temperature | cake gross weight and components | filtrate gross weight and components |
|---|---|---|---|---|
| 3 | 23.40 g<br>Geranylneryl palmitate<br>28.4% purity: 6.65 g<br>Geranylgeranyl palmitate<br>57.9% purity: 13.55 g | Toluene<br>68 g<br>−25° C. | 12.0 g<br>Geranylneryl palmitate<br>29.0% purity: 3.48 g<br>Geranylgeranyl palmitate<br>67.8% purity: 8.13 g | 13.5 g<br>Geranylneryl palmitate<br>23.5% purity: 3.17 g<br>Geranylgeranyl palmitate<br>40.0% purity: 5.40 g |
| 4 | 24.0 g | Ethanol | 14.9 g | 10.2 g |

TABLE 1-continued

| | Starting material for crystallization gross weight and components | Solvent weight filtration temperature | cake gross weight and components | filtrate gross weight and components |
|---|---|---|---|---|
| 5 | Geranylneryl myristate 36.7% purity: 8.80 g Geranylgeranyl myristate 55.0% purity: 13.20 g 11.55 g Geranylneryl laurate 38.1% purity: 4.40 g Geranylgeranyl laurate 46.7% purity: 5.39 g | 100 g −10° C. Hexane 50 g −40° C. | Geranylneryl myristate 30.9% purity: 4.60 g Geranylgeranyl myristate 59.0% purity: 8.80 g 3.10 g Geranylneryl laurate 26.8% purity: 0.83 g Geranylgeranyl laurate 67.7% purity: 2.1 g | Geranylneryl myristate 39.2% purity: 4.00 g Geranylgeranyl myristate 41.2% purity: 4.20 g 7.21 g Geranylneryl laurate 49.8% purity: 3.59 g Geranylgeranyl laurate 45.2% purity: 3.26 g |

TABLE 2

| | Starting material for crystallization gross weight and components | Solvent weight filtration temperature | cake gross weight and components | filtrate gross weight and components |
|---|---|---|---|---|
| 6 | 187.20 g Geranylneryl p-nitrobenzoate 21.2% purity: 39.76 g Geranylgeranyl p-nitrobenzoate 52.7% purity: 98.77 g | Ethanol 207.8 g −16° C. | 96.05 g Geranylneryl p-nitrobenzoate 9.1% purity: 8.73 g Geranylgeranyl p-nitrobenzoate 83.6% purity: 80.3 g | 184.29 g Geranylneryl p-nitrobenzoate 17.0% purity: 31.41 g Geranylgeranyl p-nitrobenzoate 9.1% purity: 16.70 g |
| 7 | 93.44 g Geranylneryl p-nitrobenzoate 9.1% purity: 8.50 g Geranylgeranyl p-nitrobenzoate 83.6% purity: 78.12 g | Ethanol 345 g −15° C. | 78.83 g Geranylneryl p-nitrobenzoate 1.3% purity: 1.0 g Geranylgeranyl p-nitrobenzoate 89.8% purity: 70.8 g | 361.14 g Geranylneryl p-nitrobenzoate 2.0% purity: 7.20 g Geranylgeranyl p-nitrobenzoate 2.0% purity: 7.20 g |
| 8 | 10.0 g Geranylneryl p-nitrobenzoate 21% purity: 2.1 g Geranylgeranyl p-nitrobenzoate 55.5% purity: 5.55 g | Isopropyl alcohol 50 g −20° C. | 8.1 g Geranylneryl p-nitrobenzoate 1.6% purity: 0.13 g Geranylgeranyl p-nitrobenzoate 46.9% purity: 3.8 g | 6.32 g Geranylneryl p-nitrobenzoate 31.7% purity: 2.0 g Geranylgeranyl p-nitrobenzoate 29.2% purity: 1.85 g |

TABLE 3

| | Starting material for crystallization gross weight and components | Solvent weight filtration temperature | cake gross weight and components | filtrate gross weight and components |
|---|---|---|---|---|
| 9 | 10.0 g Geranylneryl p-nitrobenzoate 21% purity: 2.1 g Geranylgeranyl p-nitrobenzoate 55.5% purity: 5.55 g | Methanol 90 g −18° C. | 5.0 g Geranylneryl p-nitrobenzoate 10.3% purity: 0.52 g Geranylgeranyl p-nitrobenzoate 85.1% purity: 4.25 g | 4.1 g Geranylneryl p-nitrobenzoate 37.8% purity: 1.55 g Geranylgeranyl p-nitrobenzoate 28.1% purity: 1.15 g |
| 10 | 19.27 g Geranylneryl p-methoxycarbonylbenzoate 28.8% purity: 5.55 g Geranylgeranyl p-methoxycarbonylbenzoate 49.0% purity: 9.45 g | Ethanol 45 g −40° C. | 14.25 g Geranylneryl p-methoxycarbonylbenzoate 34.1% purity: 4.86 g Geranylgeranyl p-methoxycarbonylbenzoate 65.2% purity: 9.14 g | 2.10 g Geranylneryl p-methoxycarbonylbenzoate 32.4% purity: 0.68 g Geranylgeranyl p-methoxycarbonylbenzoate 15.2% purity: 0.32 g |
| 11 | 17.62 g Geranylneryl m,m-Dinitrobenzoate 32.3% purity: 5.70 g Geranylgeranyl m,m-Dinitrobenzoate 47.1% purity: 8.30 g | Ethanol 100 g 3° C. | 5.20 g Geranylneryl m,m-Dinitrobenzoate 20.0% purity: 1.04 g Geranylgeranyl m,m-Dinitrobenzoate 72.3% purity: 3.76 g | 13.2 g Geranylneryl m,m-Dinitrobenzoate 34.2% purity: 4.51 g Geranylgeranyl m,m-Dinitrobenzoate 34.4% purity: 4.54 g |

TABLE 4

| | Starting material for crystallization gross weight and components | Solvent weight filtration temperature | cake gross weight and components | filtrate gross weight and components |
|---|---|---|---|---|
| 12 | 14.72 g p-nitrobenzoate ester mixture A 30.5% purity: 4.49 g Geranylgeranyl m,m-Dinitrobenzoate 25.2% purity: 3.71 g | Ethanol 58 g −15° C. | 5.1 g p-nitrobenzoate ester mixture A 15.1% purity: 0.77 g Geranylgeranyl m,m-Dinitrobenzoate 28.4% purity: 1.45 g | 8.83 g p-nitrobenzoate ester mixture A 41.9% purity: 3.70 g Geranylgeranyl m,m-Dinitrobenzoate 25.0% purity: 2.21 g |
| 13 | 4.97 g p-nitrobenzoate ester mixture A 15.1% purity: 0.75 g Geranylgeranyl m,m-Dinitrobenzoate 28.4% purity: 1.41 g | Ethanol 11.6 g −14° C. | 0.75 g p-nitrobenzoate ester mixture A 25.3% purity: 0.19 g Geranylgeranyl m,m-Dinitrobenzoate 73.6% purity: 0.53 g | 2.78 g p-nitrobenzoate ester mixture A 44.6% purity: 1.24 g Geranylgeranyl m,m-Dinitrobenzoate 31.2% purity: 0.87 g |

In Table 4, the p-nitrobenzoate ester mixture A indicated in Examples 12, 13 is one which contains the following ester derivatives. The quantitative analyses of these ester derivatives are difficult and only a total amount is shown.

3,7,11,16-tetramethyl-2Z,6Z,10Z,14-hexadecatetraene p-nitrobenzoate
3,7,11,16-tetramethyl-2E,6Z,10Z,14-hexadecatetraene p-nitrobenzoate
3,7,11,16-tetramethyl-2Z,6Z,10E,14-hexadecatetraene p-nitrobenzoate
3,7,11,16-tetramethyl-2Z,6E,10Z,14-hexadecatetraene p-nitrobenzoate
3,7,11,16-tetramethyl-2Z,6E,10E,14-hexadecatetraene p-nitrobenzoate
3,7,11,16-tetramethyl-2E,6E,10Z,14-hexadecatetraene p-nitrobenzoate
3,7,11,16-tetramethyl-2E,6Z,10E,14-hexadecatetraene p-nitrobenzoate (Conditions of HPLC analysis in the tables)

1. Analyses of geranylgeranyl palmitate, geranylgeranyl myristate and geranylgeranyl laurate
   Same as in Reference 1.
2. Analysis of geranylgeranyl p-nitrobenzoate.
   Same as in Reference 3.
3. Analyses of geranylgeranyl p-methoxycarbonylbenzoate and geranylgeranyl m,m-dinitrobenzoate
   Same as in Reference 4.

The crystallization temperatures and $^1$H-NMR data of the cakes obtained in the examples 3–13 are shown in Table 5.

TABLE 5

| No. | Crystallization temperature of cake obtained | Compound name and $^1$H-NMR DATA |
|---|---|---|
| 3 | 3° C.–3.5° C. | Geranylgeranyl palmitate NMR δ (300MHz, CDCl$_3$): 0.89(t, J=6.4Hz, 3H), 1.26(s, 26H), 1.60(S, 9H), 1.68(m, 5.1H), 1.76(br, 0.9H), 1.98–2.15(m, 12H), 2.31(m, 2H), 4.60(m, 2H), 5.11(br, 3H), 5.32(m, 1H) |
| 4 | −3° C.—−3.2° C. | Geranylgeranyl myristate NMR δ (300MHz, CDCl$_3$): 0.89(t, J=6.6Hz, 3H), 1.26(s, 22H), 1.60(S, 9H), 1.71(m, 4.05H), 1.76(br, 1.05H), 1.98–2.18(m, 12H), 2.31(m, 2H), 4.60(m, 2H), 5.11(br, 3H), 5.32(m, 1H) |
| 5 | −27° C.—−28° C. | Geranylgeranyl myristate NMR δ (300MHz, CDCl$_3$): 0.88(t, J=6.4Hz, 3H), 1.26(s, 18H), 1.60(s, 9H), 1.68(m, 5.16H), 1.76(br, 0.84H), 1.98–2.2(m, 12H), 2.30(m, 2H), 4.60(m, 2H), 5.11(br, 3H), 5.32(m, 1H) |
| 7 | 22° C.–23° C. | Geranylgeranyl p-nitrobenzoate NMR δ (300MHz, CDCl$_3$): 1.58–1.62(m, 9H), 1.67(s, 3H), 1.79(s, 3H), 1.95–2.20(m, 12H), 4.90(d, J=7.1Hz, 2H), 5.02–5.14(m, 3H), 5.48(t, J=7.1Hz, 1H), 8.18–8.32(m, 4H) |
| 10 | −3—−4° C. | Geranylgeranyl p-methoxycarbonylbenzoate NMR δ (300MHz, CDCl$_3$): 1.58–1.62(m, 9H), 1.67(s, 3H), 1.78(s, 3H), 1.95–2.20(m, 12H), 3.94(s, 3H), 4.88(d, J=7.1Hz, 2H), 5.02–5.14(m, 3H), 5.48(t, J=7.1Hz, 1H), q(d—d, J=8.91Hz, J=9.78Hz, 4H) |
| 11 | 40° C.–42° C. | Geranylgeranyl m,m-dinitrobenzoate NMR δ (300MHz, CDCl$_3$): 1.58–1.62(m, 9H), 1.68(s, 3H), 1.82(s, 3H), 1.95–2.25(m, 12H), 3.94(s, 3H), 4.98(d, J=7.4Hz, 2H), 5.02–5.14(m, 3H), 5.50(t, J=7.3Hz, 1H), 9.15–9.30(m, 3H) |
| 13 | −8° C.—−9° C. | Geranylgeranyl p-nitrobenzoate NMR δ (300MHz, CDCl$_3$): 1.58–1.62(m, 9H), 1.67(s, 3H), 1.79(s, 2.1H), 1.82–1.85(m, 0.3H), 1.95–2.20(m, 12H), 4.90(m, 2H), 5.02–5.14(m, 3H), 5.48 (m, 1H), 8.18–8.32(m, 4H) |

Example 14

(Preparation of geranylgeraniol through hydrolysis of geranylgeranyl stearate)

250 g of methanol, 4.7 g of potassium hydroxide and 10 g of water were added to 23.0 g of geranylgeranyl stearate (containing 22.08 g of geranylgeranyl stearate and 0.37 g of geranylneryl stearate) obtained as a cake in Example 2. The reaction mixture was stirred at 50° C. for 1 hour and cooled down to room temperature, to which 130 g of hexane was added. The resulting organic phase was separated, and the aqueous phase (lower phase) was washed twice with 120 g of hexane. Thereafter, the hexane washings were combined to the organic phase, followed by washing twice with 100 g of a 50% aqueous methanol. The resultant organic phase was concentrated under reduced pressure to give 12 g of crude geranylgeraniol. This crude product was subjected to simple distillation (137° C., 0.3 mmHg) to give 8.2 g of a main fraction. The results of the analysis of the obtained fraction with gas chromatography revealed that it contained geranylgeraniol with a purity of 98.1% and geranylnerol with a purity of 1.2%.

The conditions of the analysis of the gas chromatography are as follows.

Column: PEG-HT 5%, 80/100 mesh, Chromosorb WAW DMCS (made by GL Science INC.)
Oven temperature: 210° C.
Injection temperature: 240° C.
Carrier gas: nitrogen, 1.5 kg/cm$^2$
Detector: FID

Example 15

(Preparation of geranylgeraniol through hydrolysis of geranylgeranyl p-nitrobenzoate)

100 g of ethanol, 7.88 g of sodium hydroxide and 30 g of water were added to 75 g of geranylgeranyl p-nitrobenzoate (containing 0.98 g of geranylneryl p-nitrobenzoate and 67.35 g of geranylgeranyl p-nitrobenzoate) obtained as a cake in Example 7. The reaction mixture was stirred at 50°C. for 2 hours and cooled down to room temperature, to which 300 g of toluene and 200 g of water were added. The resulting organic phase was separated and washed twice with 200 g of water, and concentrated under reduced pressure to give 55 g of crude geranylgeraniol. This crude product was subjected to simple distillation (154°C., 0.5 mmHg) to give 42.1 g of a main fraction. The results of the analysis of the obtained fraction with gas chromatography under the same conditions as in Example 14 revealed that it contained geranylgeraniol with a purity of 97.8% and geranylnerol with a purity of 1.2%.

Obviously, numerous modifications and variations are possible in light of the above teachings. It is therefore to be understood that within the scope of the appended claims the present invention may be practiced otherwise than as specifically described herein.

What is claimed is:

1. A process for producing 3,7,11,15-tetramethylhexadeca-2E,6E,10E,14-tetraenol comprising the steps of dissolving at least one ester derivative wherein one or more carbon-carbon double bonds in the molecule are in cis form represented by the general formula (1):

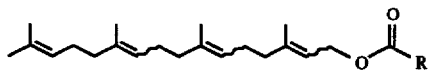

wherein R represents an aromatic group which can be substituted with at least one substituent, or a higher aliphatic group having from 7 to 25 carbon atoms, and wavy lines, respectively, represent a state where each carbon-carbon double bond can be present in cis or trans form, and an ester derivative of the general formula (2):

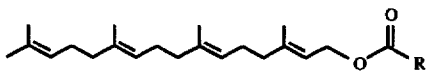

wherein R is as defined above, in an organic solvent, and gradually cooling the resultant solution to permit crystals to precipitate so as to selectively crystallize said esters in order to selectively obtain the ester derivative of the formula (2), and hydrolyzing the thus obtained ester derivative at a temperature in the range of 0° C. to 150° C.

2. A process according to claim 1, characterized in that R in the formulae (1) and (2) is an aromatic group which can be substituted with at least one substituent selected from the group consisting of a methyl group, an ethyl group, a n-propyl group, an i-propyl group, a n-butyl group, a t-butyl group, a chlorine atom, a bromine atom, an iodine atom, a carboxyl group, a methoxycarbonyl group, an ethoxycarbonyl group, an acetyl group, a benzoyl group, a methoxy group, an ethoxy group, a nitrile group, a nitro group, a methylsulfonyl group, an ethylsulfonyl group, a p-toluenesulfonyl group, a phenylsulfonyl group, an amino group, a dimethylamino group, a methylaminogroup, an ethylamino group and a hydroxy group.

3. A process according to claim 1, characterized in that R is a higher aliphatic group selected from the group consisting of a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-icosyl group, a henicosyl group, a 1-decenyl group, an 8-hexadecenyl group, an 8,11-heptadecadienyl group and a 1-undecynyl group.

4. A process according to claim 1, characterized in that the crystallization is carried out in at least one solvent selected from the group consisting of methanol, ethanol, i-propanol, n-butanol, methyl cellosolve, n-hexane, cyclohexane, n-heptane, benzene, toluene, xylene, methylene chloride, chloroform, ethyl acetate, butyl acetate, diethyl ether, i-propyl ether and methyl t-butyl ether.

5. A process according to claim 1, characterized in that the crystallization is carried out in at least one solvent selected from the group consisting of methanol, ethanol, i-propanol, n-butanol, n-hexane and toluene.

6. A process according to claim 1 wherein R represents an aromatic group which can be substituted with at least one substituent, said aromatic group being selected from the group consisting of phenyl, naphthyl, anthryl, pyridyl and furyl.

7. A process according to claim 1 wherein said hydrolyzation is carried out under basic hydrolyzation conditions.

8. The process of claim 7 wherein said basic conditions are achieved using an aqueous solution of alkali metal hydroxide or alkali earth metal hydroxide, said hydroxide being present in an amount of 1 to 10 mols per mol of the ester derivative of geranylgeraniol.

9. The process of claim 7 wherein said hydrolysis is carried out in an alcohol solvent.

10. The process of claim 7 wherein said alcohol solvent is selected from the group consisting of methanol, ethanol, i-propanol and n-butanol.

* * * * *

UNITED STATES PATENT AND TRADEMARK OFFICE
CERTIFICATE OF CORRECTION

PATENT NO. : 5,663,461
DATED : September 2, 1997
INVENTOR(S) : Toshiki MORI, et al.

It is certified that error appears in the above-identified patent and that said Letters Patent is hereby corrected as shown below:

On the title page, item [30], Foreign Application Priority date should be:

--Nov. 8, 1994--

Signed and Sealed this

Second Day of December, 1997

Attest:

BRUCE LEHMAN

*Attesting Officer*  *Commissioner of Patents and Trademarks*